US00PP22082P2

(12) United States Plant Patent

Klemm et al.

(10) Patent No.: US PP22,082 P2

(45) Date of Patent: Aug. 16, 2011

(54) *PELARGONIUM* PLANT NAMED 'KLEPZ09251'

(50) Latin Name: *Pelargonium zonale*
Varietal Denomination: KLEPZ09251

(75) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/798,189

(22) Filed: Mar. 31, 2010

(51) Int. Cl.
*A01H 5/00* (2006.01)

(52) U.S. Cl. ..... Plt./327

(58) Field of Classification Search ..... Plt./327
See application file for complete search history.

*Primary Examiner* — Susan McCormick Ewoldt

(74) *Attorney, Agent, or Firm* — Jondle & Associates, P.C.

(57) ABSTRACT

A new variety of *Pelargonium* named 'KLEPZ09251' particularly characterized by dark green foliage with strong leaf zonation, shiny salmon inflorescences with a lighter border, and a medium growth habit, is disclosed.

1 Drawing Sheet

Genus and species: *Pelargonium zonale.*
Variety denomination: 'KLEPZ09251'.

BACKGROUND OF THE NEW PLANT

The present invention comprises a new and distinct variety of *Pelargonium*, botanically known as *Pelargonium zonale*, and hereinafter referred to by the variety name 'KLEPZ09251'. 'KLEPZ09251' was discovered as a seedling resulting from a controlled cross in September 2004 in Stuttgart, Germany between the proprietary female *Pelargonium* parent, 'Pisa kleaspia' (unpatented) and the proprietary male *Pelargonium* parent, 'SI 015' (unpatented). A single plant selection was subsequently chosen for further evaluation and for asexual propagation.

The new variety was first propagated via vegetative cuttings in June 2005 in Stuttgart, Germany and has been asexually reproduced repeatedly by vegetative cuttings in Stuttgart, Germany for approximately six to seven generations. 'KLEPZ09251' has been found to retain its distinctive characteristics through successive asexual propagations via vegetative cuttings.

Plant Breeder's Rights for this variety were applied for in Canada on Mar. 25, 2009. 'KLEPZ09251' has not been made publicly available or sold more than one year prior to the filing date of this application.

SUMMARY OF THE INVENTION

The following are the most outstanding and distinguishing characteristics of this new variety when grown under normal commercial practices in a greenhouse in Stuttgart, Germany.

1. Dark green foliage with strong leaf zonation;
2. Shiny salmon inflorescences with a lighter border; and
3. A medium growth habit.

DESCRIPTION OF THE PHOTOGRAPH

This new *Pelargonium* plant is illustrated by the accompanying photograph which shows blooms, buds, and foliage of the plant. The colors shown are as true as can be reasonably obtained by conventional photographic procedures. The photograph is of a 3-month-old plant taken in January through April 2009 and grown from rooted cuttings in a 12 centimeter pot in a greenhouse (glasshouse) in Stuttgart, Germany under conditions which approximate those generally used in commercial practice.

DESCRIPTION OF THE NEW VARIETY

The following detailed descriptions set forth the distinctive characteristics of 'KLEPZ09251'. The data which define these characteristics were collected from asexual reproductions carried out in Stuttgart, Germany. The plant history was taken on 3-month old, un-pinched plants grown in 12 centimeter pots in a greenhouse in January through April. The color readings were determined under natural light. Color references are to The R.H.S. Colour Chart of The Royal Horticultural Society of London (R.H.S.), Fifth Edition (2007).

DETAILED BOTANICAL DESCRIPTION OF THE NEW PLANT

Classification:
- *Family.*—Geraniacaea.
- *Species.*—*Pelargonium zonale.*
- *Common name.*—*Pelargonium* (Geranium).
- *Denomination.*—'KLEPZ09251'.

Parentage:
- *Female parent.*—The proprietary female *Pelargonium* parent, 'Pisa kleaspia' (unpatented).
- *Male parent.*—The proprietary male *Pelargonium* parent, 'SI 015' (unpatented).

Plant:
- *Habit.*—Upright.
- *Height.*—20.0 cm to 22.0 cm.
- *Spread.*—20.0 cm.
- *Life cycle.*—Spring to autumn.
- *Form.*—Rounded, bushy.
- *Time to produce a rooted cutting.*—18 days.
- *Time to bloom from propagation.*—Approximately 75 days.

*Lastingness of inflorescence on the plant.*—10 to 14 days.

Stems:

*Stem color.*—RHS 146B to RHS N199A.
*Pubescence.*—Present and very short.
*Stem form.*—Round.
*Diameter.*—0.5 cm to 1.0 cm.
*Length.*—10.0 cm to 20.0 cm.
*Internode length.*—0.8 cm to 2.0 cm.

Leaves:

*Arrangement.*—Alternate.
*Shape.*—Kidney-shaped-round.
*Apex.*—Round.
*Base.*—Closed to open.
*Margin.*—Entire to crenate.
*Surface texture* (*both upper and lower surfaces*).—Dull.
*Length.*—5.0 cm to 10.0 cm.
*Width.*—6.0 cm to 12.0 cm.
*Color.*—Upper surface: RHS 147A. Lower surface: RHS 137A.
*Surface pubescence.*—Slightly rough.
*Petiole.*—Length: 4.0 cm to 8.0 cm. Color: RHS 146B and RHS N199A.
*Venation pattern.*—Palmate.
*Venation color.*—RHS 137B.

Inflorescence:

*Umbels.*—Length: 6.0 cm to 9.0 cm. Diameter: 7.0 cm to 10.0 cm.
*Individual florets of the umbel.*—Depth: 2.0 cm. Diameter: 4.0 cm.
*Fragrance.*—Absent.

Flower buds:

*Cluster shape.*—Round.
*Cluster size.*—Length: 0.5 cm to 1.5 cm. Width: 0.54 cm to 0.8 cm.
*Texture.*—Slightly rough.
*Bud.*—Shape: Elliptic, shell-shaped. Apex: Peaked. Base: Blunt. Margin: Entire, smooth. Color: RHS 137B and RHS N199A.

Petals:

*Quantity per flower.*—Greater than 6.
*Shape.*—Drop-shaped.
*Apex.*—Round.
*Base.*—Dull.
*Margin.*—Entire.
*Length.*—1.8 cm to 2.0 cm.
*Width.*—1.5 cm.
*Color of lobes.*—Upper lobes (both upper and lower surfaces): RHS N30B and RHS 38A. Lower lobes (both upper and lower surfaces): RHS 50D.

Sepals:

*Number per flower.*—5.
*Shape.*—Lanceolate.
*Apex.*—Acute.
*Base.*—Obtuse.
*Margin.*—Entire.
*Color* (*upper surface*).—RHS 137B.
*Length.*—0.5 cm.
*Width.*—0.3 cm.

Pedicel:

*Length.*—2.0 cm to 3.0 cm.
*Diameter.*—0.1 cm to 0.2 cm.
*Color.*—RHS N199A.

Peduncle:

*Length.*—10.0 cm to 20.0 cm.
*Diameter.*—0.4 cm to 0.6 cm.
*Color.*—RHS N199A and RHS 146B.
*Texture.*—Slightly rough.

Reproductive organs:

*Stamens.*—Anther length: 0.3 cm. Filament length: 0.6 cm. Filament color: RHS 62D. Pollen amount: Moderate. Pollen color: RHS 31B.
*Pistils.*—Number: 1. Stigma color: RHS N57A. Style length: 0.5 cm. Style color: RHS 62D. Ovary arrangement: Central, middle.

Fruit and seed set: None observed.

Disease and insect resistance: No particular disease or insect resistance observed.

COMPARISON WITH PARENTAL AND COMMERCIAL VARIETIES

'KLEPZ09251' differs from the female parent, the proprietary female *Pelargonium* parent, 'Pisa kleaspia' (unpatented), in that 'KLEPZ09251' has darker salmon-colored flowers and a medium growth habit, while 'Pisa kleaspia' has a light salmon-colored flowers color and a very compact growth habit.

'KLEPZ09251' differs from the male parent, the proprietary male *Pelargonium* parent, 'SI 015' (unpatented), in that 'KLEPZ09251' has strong leaf zonation, while 'SI 015' has medium leaf zonation. In addition, 'KLEPZ09251' has a medium growth habit, while 'SI 015' has a strong growth habit.

'KLEPZ09251' differs from the commercial comparison variety 'FISROLAMON' (U.S. Plant Pat. No. 19,076), in that 'KLEPZ09251' has salmon flowers and a medium growth habit, while 'FISROLAMON' has salmon-orange flowers and a moderately vigorous growth habit. In addition, 'KLEPZ09251' has dark green foliage with strong leaf zonation, while 'FISROLAMON' has medium green foliage with medium to strong leaf zonation.

We claim:

1. A new and distinct variety of *Pelargonium* plant named 'KLEPZ09251' as shown and described herein.

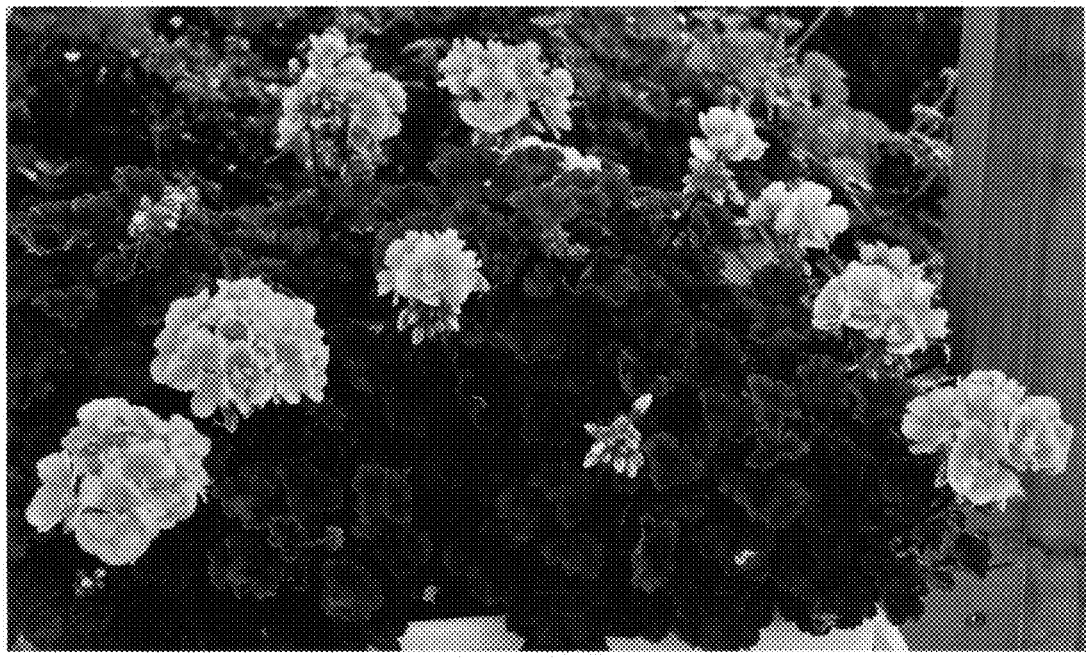

* * * * *